United States Patent [19]

Dolle, III et al.

[11] Patent Number: 5,734,054
[45] Date of Patent: Mar. 31, 1998

[54] HYDROXY-AMINO ACID AMIDES

[75] Inventors: Roland Ellwood Dolle, III, King of Prussia, Pa.; Theodore O. Johnson, Jr., Plainsboro, N.J.; Carolyn DiIanni Carroll, Yardley, Pa.

[73] Assignee: Pharmacopeia, Inc., Princeton, N.J.

[21] Appl. No.: 743,944

[22] Filed: Nov. 5, 1996

[51] Int. Cl.$^6$ .................. C07D 241/04; C07D 295/00
[52] U.S. Cl. ............................ 544/390; 544/400
[58] Field of Search ..................... 544/390, 400

[56] References Cited

U.S. PATENT DOCUMENTS 5,120,718  6/1992  Goldman et al. ................. 514/32

OTHER PUBLICATIONS

Rich et al., "Design and Discovery of Aspartyl Protease Inhibitors Mechanistic and Clinical Implications". In Conformationally Directed Drug Design, Julius A. Vida and Maxwell Gordon, eds. ACS Symposium Series, American Chemical Society, Washington, D.C., Chapter 10, pp. 211–237, 1984.

Primary Examiner—Mukund J. Shah
Assistant Examiner—Bruck Kifle
Attorney, Agent, or Firm—Heslin & Rothenberg, P.C.

[57] ABSTRACT

Compounds of Formula I

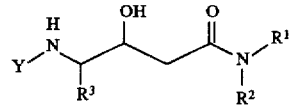

are disclosed as inhibitors of plasmepsin and cathepsin D. The compounds are therefore useful to treat diseases such as malaria. In preferred compounds of formula I, Y is the residue of an N-acylated amino acid, a substituted 4-aminoproline or a substituted piperazinealkanoic acid. Intermediates in the solid phase synthesis of compounds of formula I, in which the compounds are attached to a solid support, are also disclosed.

7 Claims, No Drawings

HYDROXY-AMINO ACID AMIDES

FIELD OF THE INVENTION

The present invention relates to amino acid (statine) analogs that display selective inhibitory activity against plasmepsin and cathepsin D.

BACKGROUND OF THE INVENTION

Resistance to known antimalarial therapies is becoming an increasing problem and new therapies are therefore desperately needed. Upon infecting a host, the malaria parasite avidly consumes the host hemoglobin as its source of nutrients. Plasmepsin I and II are proteases from *Plasmodium falciparum* that are necessary during the initial stages of hemoglobin hydrolysis and digestion, which primarily occurs in the α-chain, between Phe 33 and Leu 34, although other sites may serve as substrates for hydrolysis as well. It has been shown in cultures inhibition of plasmepsin by a peptidomimetic inhibitor is effective in preventing malarial hemoglobin degradation and in killing the parasite (Francis, S. E., Gluzman, I. Y. Oksman, A., Knickerbocker, A., Mueller, Bryant, M. L., Sherman, D. R., Russell, D. G., and Goldberg, D. E. (1994) EMBO J. 13, 306–317). Thus, persons of skill in the art expect that plasmepsin inhibitors will provide effective antimalarial therapy.

Cathepsin D is a human protease in the endosomal-lysosomal pathway, involved in lysosomal biogenesis and protein targeting, and may also be involved in antigen processing and presentation of peptide fragments. The protease therefore displays broad substrate specificity but prefers hydrophobic residues on either side of the scissile bond.

Cathepsin D has been implicated in a variety of diseases, including corrective tissue disease, muscular dystrophy, and breast cancer. Most recently, cathepsin D is believed to be γ-secretase, the protease which processes the β-amyloid precursor protein to generate the C-terminus of β-amyloid (Dreyer, R. N., Bausch, K. M., Fracasso, P., Hammond, L. J., Wunderlich, D., Wirak, D. O., Davis, G., Brini, C. M., Bucholz, T. M., Konig, G., Kamark, M. E., and Tamburini, P. P. (1994) Eur. J. Biochem., 224, 265–271 and Ladror, U. S., Synder, S. W., Wang, G. T., Holzman, and Krafft, G. A. (1994) J. Biol. Chem., 269, 18422–18428), which is the major component of plaque in the brains of Alzheimer's patients. Consequently, persons of skill in the art expect that inhibitors of cathepsin D will be useful in treating Alzheimer's disease.

The present invention relates to amino acid (statine) analogs and their inhibitory action against aspartyl proteases, and more particularly, the invention relates to the identification of amino acid analogs that display selective inhibitory activity against plasmepsin and cathepsin D. Although statine-containing peptides are known which inhibit aspartyl proteases (Shewale, J. G.; Takahashi, R.; Tang, J., Aspartic Proteinases and Their Inhibitors, Kostka, V., Ed. Wlater de Gruyter: Berlin (1986) pp 101–116), there are only a few selective inhibitors for cathepsin D (Lin, T. Y.; Williams, H. R., Inhibition of Cathepsin D by Synthetic Oligopeptides, *J. Biol. Chem.* (1979), 254, 11875–11883; Rich, D. H.; Agarwal, N. S., Inhibition of Cathepsin D by Substrate Analogues Containing Statine and by Analogues of Pepstatin, *J. Med. Chem.* (1986) 29 (2519–2524), and for plasmepsin (Silva, A. M. et al., Structure and Inhibition of Plasmepsin II, A Hemoglobin-Degrading Enzyme From *Plasmodium falciparum*, Proceed Natl Acad Sci, 1996, 93, 10034–10039). The present invention also relates to the solid phase synthesis of such amino acid analogs.

SUMMARY OF THE INVENTION

I. Preferred Embodiments

The compounds of the present invention are represented by Formula I:

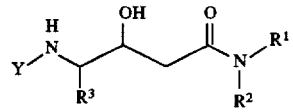

wherein:

$R^1$ and $R^3$ are independently chosen from the group consisting of alky, alkoxyalkyl and arylalkyl;

$R^2$ is H or ⓢ—C(O)—L— wherein:

ⓢ is a solid support; and

—L— is a linker; and

Y is —Aa—C(O)$R^4$ or —C(O)$R^5$;

wherein

Aa is an amino acid attached via its carboxyl to the amine nitrogen of structure I;

$R^4$ is chosen from the group consisting of alkyl, aryl, substituted alkyl, cycloalkyl, substituted cycloalkyl, heterocycloalkyl or substituted heterocycloalkyl; and $R^5$ is

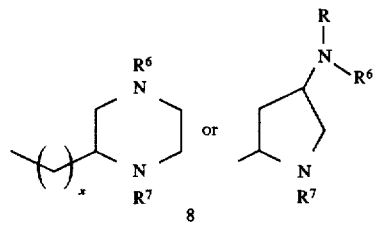

wherein x is 0 or 1;

$R^6$ and $R^7$ are independently chosen from the group consisting of substituted alkyl, alkylcarbonyl and substituted alkylcarbonyl; and $R^8$ is alkyl.

Preferred compounds of Formula I are those wherein —L— is of Formula (a)

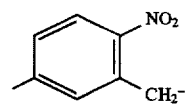

(a)

wherein the left-hand bond is the point of attachment to —C(O)— and the right hand bond is the point of attachment to the amide nitrogen of structure I.

A preferred embodiment of the invention are compounds of Formula I wherein:

$R^1$ is chosen from the group consisting of butyl, 3-phenylpropyl and 3-methoxypropyl;

Y is —Aa—C(O)$R^4$;

Aa is chosen from the group consisting of valine, leucine, phenylalanine, isoleucine β-2-thienylalanine, t-butylglycine, cysteine and phenylglycine; and $R^4$ is chosen from the group consisting of

[structures: ethyl-naphthalene; 4-methylbenzyl-pyrrolidine; methylcyclohexyl; 4-methylbenzyl-NHCH₃; dimethoxy-methylbenzene (OCH₃, OCH₃); ethoxy-naphthalene; butyloxy-2,4-dichlorobenzene; heptyl-CH₃; 4-ethylphenoxy-malonic acid (O-CH(COOH)-COOH); piperidinyl-CONH₂-phenyl]

Another preferred embodiment of the invention are compounds of Formula I wherein:

$R^1$ is chosen from the group consisting of methyl, benzyl, butyl, 3-phenylpropyl, 3-methoxypropyl, 2-pyridinylmethyl and 3-pyridinylmethyl;

Y is —C(O)R⁵;

$R^6$ is chosen from the group consisting of 3-pyridinylmethyl, phenylethoxyethyl, 3,4,5-trimethoxybenzyl, 4-acetamidobenzyl, 4-phenylbutyl, 3,4-dichlorobenzyl, 4-phenylbenzyl, 3-phenylpropyl, 3,5-bis(trifluoromethyl)benzyl, 3-phenylpropionyl, isobutyl, propionyl and 3,5-di (trifluoromethyl) phenylacetyl; and $R^7$ is chosen from the group consisting of 4-isopropoxybenzoyl, nicotinoyl, 3,4,5-trimethoxybenzoyl, 3-phenoxybenzoyl, 3-(2-methoxyphenyl)propyl, 3,4,5-trimethoxyphenylpropionyl, 3,3-diphenylpropionyl, phenylacetyl, 3,4-dichlorophenylacetyl and ethyl adipoyl.

A preferred subset of the foregoing embodiment of the invention are compounds of the Formula I wherein:

$R^1$ is chosen from the group consisting of methyl, benzyl, butyl, 3-phenylpropyl and 3-methoxypropyl;

Y is —C(O)R⁵;

$R^5$ is

[structure with R⁶-N and N-R⁷ on a ring with subscript x]

$R^6$ is chosen from the group consisting of 3-pyridinylmethyl, phenylethoxyethyl, 3,4,5-trimethoxybenzyl, 4-acetamidobenzyl, 4-phenylbutyl, 3,4-dichlorobenzyl, 4-phenylbenzyl, 3,5-bis(trifluoromethyl)benzyl, 3-phenylpropionyl and 3-phenylpropyl; and $R^7$ is chosen from the group consisting of 4-isopropoxybenzoyl, nicotinoyl, 3,4,5-trimethoxybenzoyl, 3-phenoxybenzoyl, 3-(2-methoxyphenyl)propyl, 3,4,5-trimethoxyphenylpropionyl, 3,3-diphenylpropionyl, 3,4-dichlorophenylacetyl and ethyl adipoyl.

A second subset of the second preferred embodiment of the invention are compounds of Formula I wherein $R^1$ is chosen from the group consisting of butyl, 2-pyridinylmethyl and 3-pyridinylmethyl;

$R^5$ is

[structure with R⁸-N-R⁶ branching, with N-R⁷]

$R^6$ is chosen from the group consisting of 4-phenylbenzyl, isobutyl, propionyl and 3,5-di (trifluoromethyl)phenylacetyl;

$R^7$ is chosen from the group consisting of phenylacetyl, 3-phenoxybenzoyl and 3,3-diphenylpropionyl; and $R^8$ is ethyl.

Another aspect of the invention is the use of divinylbenzene-cross-linked, polyethyleneglycol-grafted polystyrene beads optionally functionalized with amino groups (e.g., TentaGel™ S NH₂, Rapp Polymere) as the solid supports for constructing compounds of Formula I.

DETAILED DESCRIPTION OF THE INVENTION

II. Abbreviations and Definitions

The following abbreviations and terms have the indicated meaning throughout:

Alloc=allyloxy carbonyl
Bn=benzyl
BNB=4-bromomethyl-3-nitrobenzoic acid
BOC=t-butyloxy carbonyl
Bu=butyl
c-=cyclo
DCM=Dichloromethane=methylene chloride=CH₂Cl₂
DIC=diisopropylcarbodiimide
DIEA=diisopropylethyl amine
DMAP=4-N,N-dimethylaminopyridine
DMF=N,N-dimethylformamide
DVB=1,4-divinylbenzene
Et=ethyl
Fmoc=9-fluorenylmethoxycarbonyl
HATU=O-(7-Azabenzotriazol-1-yl)1,1,3,3-tetramethyluroniumhexafluorophosphate
HOAc=acetic acid
HOBt=hydroxybenzotriazole
m-=meta
Me=methyl
N₃=azido
NaBH₃CN=sodium cyanoborohydride=SCB
PEG=polyethylene glycol Ph=phenyl
s-=secondary
t-=tertiary
TFA=trifluoroacetic acid
THF=tetrahydrofuran "Alkyl" is intended to include linear, branched, or cyclic hydrocarbon structures and combinations thereof. "Lower alkyl" means alkyl groups of from 1 to 8 carbon atoms. Examples of lower alkyl groups include methyl, ethyl, propyl, isopropyl, butyl, s-and t-butyl, pentyl hexyl, octyl, cyclopropylenthyl, bornyl and the like. Preferred alkyl groups are those of $C_{20}$ or below. "Cycloalkyl" is a subset of alkyl and includes cyclic hydrocarbon groups of from 3 to 8 carbon atoms. Examples of lower cycloalkyl groups include c-propyl, c-butyl, c-pentyl, norbornyl and the like.

"Alkenyl" includes $C_2-C_8$ unsaturated hydrocarbons of a linear, branched, or cyclic ($C_5-C_6$) configuration and combinations thereof. Examples of alkenyl groups include vinyl, allyl, isopropenyl, pentenyl, hexenyl, c-hexenyl, 1-propenyl, 2-butenyl, 2-methyl-2-butenyl and the like.

"Alkynyl" includes $C_2-C_8$ hydrocarbons of a linear or branched configuration and combinations thereof containing at least one carbon-carbon triple bond. Examples of alkynyl groups include ethane, propyne, butyne, pentyne, 3-methyl-1-butyne, 3,3-dimethyl-1-butyne and the like.

"Alkoxy" refers to groups of from 1 to 8 carbon atoms of a straight, branched, cyclic configuration and combinations thereof. Examples include methoxy, ethoxy, propoxy, isopropoxy, cyclopropyloxy, cyclohexyloxy and the like.

"Acylamino" refers to acylamino groups of from 1 to 8 carbon atoms of a straight, branched or cyclic configuration and combinations thereof. Examples include acetylamino, butylamino, cyclohexylamino and the like.

"Halogen" includes F, Cl, Br, and I.

"Aryl" and "heteroaryl" mean a 5- or 6-membered aromatic or heteroaromatic ring containing 0–3 heteroatoms selected form O, N, and S; a bicyclic 9- or 10-membered aromatic or heteroaromatic ring system containing 0–3 heteroatoms selected from O, N, and S; or a tricyclic 13- or 14-membered aromatic or heteroaromatic ring system containing 0–3 heteroatoms selected from O, N, and S; each of which rings is optionally substituted with 1–3 lower alkyl, substituted alkyl, substituted alkynyl, =O, —$NO_2$, halogen, hydroxy, alkoxy, $OCH(COOH)_2$, cyano, $NR^{10}R^{10}$, acylamino, phenyl, benzyl, phenoxy, benzyloxy, heteroaryl, and heteroaryl or heteroaryloxy; each of said phenyl, benzyl, phenoxy, benzyloxy, heteroaryl, and heteroaryloxy is optionally substituted with 1–3 substituents selected from lower alkyl, alkenyl, alkynyl, halogen, hydroxy, alkoxy, cyano, phenyl, benzyl, benzyloxy, carboxamido, heteroaryl, heteroaryloxy, $NO_2$, and $NR^{10}R^{10}$;

$R^{10}$ is independently let, lower alkyl or cycloalkyl, and —$R^{10}R^{10}$ may be fused to form a cyclic ring with nitrogen.

The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole, and pyrazole.

"Arylalkyl" means an alkyl residue attached to an aryl ring. Examples include, e.g., benzyl, phenethyl and the like.

"Heteroarylalkyl" means an alkyl residue attached to a heteroaryl ring. Examples include, e.g., pyridinylmethyl, pyrimidinylethyl and the like.

"teterocycloalkyl" means a cycloalkyl where one to two of the methylene ($CH_2$) groups is replaced by a heteroatom such as O, NR' (wherein R' is H or alkyl), S or the like; with the proviso that when two heteroatoms are present, they must be separated by at least two carbon atoms. Examples of heterocycloalkyls include tetrahydrofuranyl, piperidine, dioxanyl and the like.

"Carboxyalkyl" means —C(O)R", wherein R" is alkyl.

"Substituted" alkyl, alkenyl, alkynyl, cycloalkyl, or heterocycloalkyl means alkyl, alkenyl, alkynyl, cycloalkyl or heterocycloalkyl wherein up to three H atoms on each C atom therein are replaced with halogen, hydroxy, loweralkoxy, carboxy, carboalkoxy, carboxamido, cyano, carbonyl, $NO_2$, $NR^9R^9$ (wherein $R^9$ is H, alkyl or arylalkyl), alkylthio, sulfoxide, sulfone, acylamino, amidino, phenyl, benzyl, heteroaryl, phenoxy, benzyloxy, heteroaryloxy, and substituted phenyl, benzyl, heteroaryl, phenoxy, benzyloxy or heteroaryloxy.

Aa represents an amino acid and is intended to include the racemates and all optical isomers thereof. The amino acid side chains of Aa include, e.g., methyl (alanine), hydroxymethyl (serine), phenylmethyl (phenylalanine), thiomethyl (cysteine), carboxyethyl (glutamic acid), etc. Primary and secondary amino acids are intended to include alanine, asparagine, N-β-trityl-asparagine, aspartic acid, aspartic acid-β-t-butyl ester, arginine, $N^g$-Mtr-arginine, cysteine, S-trityl-cysteine, glutamic acid, glutamic acid-γ-t-butyl ester, glutamine, N-γ-trityl-glutamine, glycine, histidine, $N^{im}$-trityl-histidine, isoleucine, leucine, lysine, $N^ε$-Boc-lysine, methionine, phenylalanine, proline, serine, O-t-butyl-serine, threonine, tryptophan, $N^{in}$-Boc-tryptophan, tyrosine, valine, sarcosine, L-alanine, chloro-L-alanine, 2-aminoisobutyric acid, 2-(methylamino)isobutyric acid, D, L-3-aminoisobutyric acid, (R)-(−)-2 aminoisobutyric acid, (S)-(+)-2-aminoisobutyric acid, 2-thienyalanine, D-norvaline, L-norvaline, L-2-amino-4-pentenoic acid, D-isoleucine, L-isoleucine, D-norleucine, 2,3-diaminopropionic acid, L-norleucine, D,L-2-aminocaprylic acid β-alanine, D,L-3-aminobutyric acid, 4-aminobutyric acid, 4-(methylamino)butyric acid, 5-aminovaleric acid, 5-aminocaproic acid, 7-aminoheptanoic acid, 8-aminocaprylic acid, 11-aminodecanoic acid, 12-aminododecanoic acid, carboxymethoxylamine, D-serine, D-homoserine, L-homoserine, D-allothreonine, L-allothreonine, D-threonine, L-threonine, D,L-4-amino-3-hydroxybutyric acid, D,L-3-hyroxynorvaline, (3S,4S)-(−)-statine, 5-hydroxy-D,L-lysine, 1-amino-1-cyclopropanecarboxylic acid, 1-amino-1-cyclopentanecarboxylic acid, 1-amino-1-cyclohexanecarboxylic acid, 5-amino-1,3-cyclohexadiene-1-carboxylic acid, 2-amino-2-norbornanecarboxylic acid, (S)-(−)-2-azetidinecarboxylic acid, cis-4-hydroxy-D-proline, cis-4-hydroxy-L-proline, trans-4-hydroxy-L-proline, 3-4-dehydro-D,L-proline, 3,4-dehydro-L-proline, pipecolic acid, pipecolinic acid, nipecotic acid, isonipecotic acid, mimosine, citrulline, 2,3-diaminopropionic acid, D,L-2,4-diaminobutyric acid, (S)-(+)-diaminobutyric acid, ornithine, 2-methylornithine, N-ε-methyl-L-lysine, N-methyl-D-aspartic acid, D,L-2-methylglutamic, D,L-2-aminoadipic acid, D-2-aminoadipic acid, naphthylalanine, L-2-aminoadipic acid, (+/−)-3-aminoadipic acid, D-cysteine, D-penicillamine, L -penicillamine, D,L-homocysteine, S-methyl-L-cysteine, L-methionine, D-ethionine, L-ethionine, S-carboxymethyl-L-cysteine, (S)-(+)-2-phenylglycine, (R)-(−)-2-phenylglycine, N-phenylglycine, N-(4-hydroxyphenyl)glycine, D-phenylalanine, (S)-(−)indoline-2-carboxylic acid, α-methyl.D,L-phenylalanine, β-methyl-D,L-phenylalanine, D-homophenylalanine, L-homophenylalanine, D,L-2- fluorophenylglycine, D,L-2-fluorophenylalanine, D,L-3-fluorophenylalanine, D,L-4-fluorophenylalanine, D,L-4-chlorophenylalanine, L-4-chlorophenylalanine, 4-bromo-D, L-phenylalanine, 4-iodo-D-phenylalanine, 3,3', 5-triiodo-L-thyronine, (+)-3,3', 5-triiodo-L-thyronine sodium salt, D-thyronine, L-thyronine, D,L-m-tyrosine, D-4-hydroxyphenylglycine, D-tyrosine, L-tyrosine, o-methyl-L-tyrosine, 3-fluoro-D,L-tyrosine, 3-iodo-L-tyrosine, 3-nitro-L-tyrosine, 3,5-diiodo-L-tyrosine, D,L-dopa, L-dopa, 2,4,5-trihydroxyphenyl-D,L-alanine, 3-amino-L-tyrosine, 4-amino-D-phenylalanine, 4-amino-L-phenylalanine, 4-amino-D,L-phenylalanine, 4-nitro-L-phenylalanine, 4-nitro-D,L-phenylalanine, 3,5-dinitro-L-tyrosine, D,L-α-methyltyrosine, L-α-methyltyrosine, (−)-3-(3,4-dihydroxyphenyl)-2-methyl-L-alanine, D,L-threo-3-phenylserine, trans-4-(aminomethyl)cyclohexane carboxylic acid, 4-(aminomethyl) benzoic acid, D,L-3-aminobutyric acid, 3- aminocyclohexane carboxylic acid, cis-2-amino-1-cyclohexane carboxylic acid, γ-amino-β-(p-chlorophenyl) butyric acid (Baclofen), D,L-3-aminophenylpropionic acid, 3-amino-3-(4-chlorophenyl) propionic acid, 3-amino-3-(2-nitrophenyl)propionic acid, cyclohexylalanine, t-butylglycine, pyridylalanine and 3-amino-4,4,4-trifluorobutyric acid.

The statine residues used in this invention were prepared by the method of Rich (Rich et al., *J. Org. Chem.*, 43, 3624 (1978)).

The material upon which the combinatorial syntheses of the invention are performed are referred to as solid supports, beads or resins. These terms are intended to include beads, pellets, disks, fibers, gels, or particles such as cellulose beads, poreglass beads, silica gels, polystyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and soluble supports such as low molecular weight non-cross-linked polystyrene.

III. Optical Isomers-Diastereomers-Geometric Isomers

Some of the compounds described herein contain one or more asymmetric centers and may thus give rise to enantiomers, diastereomers, and other stereoisometric forms which may be defined in terms of absolute stereochemistry as (R)- or (S)- , or as (D)- or (L)- for amino acids. The present invention is meant to include all such possible diastereomers, as well as their racemic and optically pure forms. Optically active (R)- and (S), or (D)- and (L)- isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are intended to be included.

IV. Assays for Determining Biological Activity

1. Method for Plasmepsin II

The assay mix contained 50 mM sodium acetate (pH 5.0), 1 mg/ml BSA, 0.01% Tween 20, 12.5% glycerol, 18 % DMSO and 12 µM plasmepsin substrate. Twenty five µL of the assay mix was added to each well of a 96-well microtiter plate containing dried down bead eluate or empty control wells. The plates were then sonicated and mixed. 25 µL of 8 nM plasmepsin II, in 50 mM sodium acetate (pH 5.0), 1 mg/ml BSA, 0.01% Tween 20, and 12.5% glycerol, was added to the assay mix. The final concentrations were 4 nM plasmepsin II, 6 µM plasmepsin substrate, 9% DMSO, 50 mM sodium acetate (pH 5.0), 1 mg/ml BSA, 0.01% Tween 20, and 12.5% glycerol. The reaction was incubated for 10 minutes at 25° C. and then quenched by the addition of 25 µL of 1M Tris (pH 8.5) and 50 % DMSO to achieve a final concentration of 0.33M Tris and 23% DMSO. The EDANS fluorescence was measured using a Tecan, SLT FluoStar fluorescence plate reader with an excitation filter of 350 nm and an emission filter 510 nm. The background was determined by 25 µL of 50 mM sodium acetate (pH 5.0), 1 mg/ml BSA, 0.01% Tween 20, and 12.5% glycerol without enzyme.

2. Method for Cathepsin D

The assay mix contained 25 mM sodium formate (pH 3.5), 1 mg/ml BSA, 12% DMSO and 12 µM cathepsin D substrate. Twenty five µL of the assay mix were added to each well of a 96-well microliter plate containing dried down bead eluate or empty control wells. The plates were then sonicated and mixed. 25 µL of 1.6 nM cathepsin D, in 25 mM sodium formate (pH 3.5), and 1 mg/ml BSA, was added to the assay mix. The final concentrations were 0.8 nM cathepsin D, 6 µM cathepsin D substrate, 6% DMSO, 25 mM sodium formate (pH 3.5), and 1 mg/ml BSA. The reaction was incubated for 10 minutes at 25° C. and then quenched by the addition of 25 µL of 1M Tris (pH 8.5) and 50% DMSO to achieve a final concentration of 0.33 M Tris and 21% DMSO. The EDANS fluorescence was measured as stated herein above. The background was determined by 25 µL of 50 mM sodium formate (pH 3.5), and 1 mg/ml BSA without enzyme.

V. Methods of Synthesis

The compounds of the present invention may be prepared according to the following methods. In carrying out the syntheses, one typically begins with a quantity of solid support that will provide enough compound after cleavage from the solid support for biological testing in the herein described assays. In the case where the solid support is TentaGel™, it is recommended that approximately 0.5 g of beads of about 180 microns in diameter, with a loading capacity of about 300 picoM per bead, be used. As the chemical yield of compounds after photolysis typically ranges from approximately 20% up to 60%, this quantity will provide a yield (approximately>10 mg) sufficient for biological testing in the given protease assays. For actual synthesis, the appropriate reagents and reaction conditions are applied to a reaction vessel containing the specified quantity of beads. During the syntheses, the beads may be washed free of any excess reagents or by-products before proceeding to the next reaction. At the end of a given reaction sequence, the beads are suspended in a suitable solvent such as methanol and exposed to UV light (365 nm) for 3 hours at room temperature. This protocol releases the compounds of Formula I (wherein $R^2$ is H) for purification and biological testing.

A. Scheme 1: Derivatizing resin with bis-Boc lysine

A batch of amino-functionalized PEG-grafted polystyrene beads 3, e.g., TentaGel™ 3 amine may be modified with bis-Boc lysine 2 to increase the available reaction sites for ligand attachment. Bis-Boc lysine 2 is coupled to the amino-functionalized beads 3 by amide bond formation. Coupling is achieved by reacting a suspension of beads in DCM and adding 2, HOBt and DIC. The suspension is shaken overnight, drained or filtered, and then washed in succession with DMF, MeOH and DCM, yielding derivatized resin 1 which is then dried overnight under vacuum.

B. Scheme 2

The various amine choices (see Tables 1 and 2) are added to the reaction vessel containing resin 1. The amines are attached to resin 1 through the photo-labile linker, 4-bromomethyl-3-nitrobenzoic acid. This attachment is accomplished in two steps.

Step 1. The Boc protecting group on resin 1 is removed and the BNB is attached by the following method. A suspension of resin 1 in 1:1 TFA/DCM is shaken for about 1 hour, then washed with DCM, MeOH, 4:1 MeOH/Et$_3$N, MeOH, DMF and then DCM. The resultant bis-amine resin 4 is suspended in DCM, and treated with a solution of BNB, HOBt and DIC in DCM. The suspension is shaken for about 3 hours, then drained and washed with DCM. The BNB resin 6 is dried overnight under vacuum.

Step 2. The BNB resin 6 from step 1 are reacted with a unique primary amine (see Tables 1 and 2) to generate compound 7. The coupling of the amine to resin 6 occurs through displacement of the linker bromide and formation of a new carbon-nitrogen bond. As a quality control for the reaction in this step, a small portion of each batch of resin may be removed and titrated with picric acid to determine the extent of amine loading.

C. Scheme 3

Amine 7 is then treated with one of the hydroxy-amino acid reagents (statines) 8 (see Tables 1 and 2). Each hydroxy-amino acid 8 is coupled to amine resin 7 by amide bond formation to produce compound 9.

Compounds 9 may be directed through either the chemistry of Schemes 4 and 5, yielding compounds as in Example 1 and found in Table 1, or in the alternative, through the chemistry of Schemes 6, 7 and 8, yielding compounds as in Example 2 and Table 2.

D. Scheme 4 (With Scheme 5, yields compounds as in Example 1)

Resin 9 is treated with TFA/DCM to remove the Boc protecting group, thus exposing the terminal amino group and forming compounds 10. Each reaction vessel is then treated with one amino acid 11 (see Table 1), for separate coupling of each amino acid to compound 10 by amide bond formation to produce compounds 12. The amino acids are introduced with the base-labile Fmoc on the alpha-nitrogen atom.

E. Scheme 5

Compounds 12 are treated with piperidine/DMF to deprotect the amino group by removing the Fmoc protecting group, thus giving rise to compounds 13, which in turn are treated with one carboxylic acid (see Table 1), which couples with compound 13 to generate compounds 14. Resin 14 may be cleaved by exposing it to UV light (ca. 360 nm) for 15–180 minutes at 25°–50° C. in a suitable solvent such as methanol to produce amides of Formula I (wherein $R^2$ is H), as in Example 1 and Table 1.

Scheme 6 (With Schemes 7 and 8, yields compounds as in Example 2)

Resin 9 (from Scheme 3) is treated with TFA/DCM to remove the Boc protecting group, thus exposing the terminal amino group and forming compounds 10. The compound is then treated with one diamino acid 17 (Table 2), for separate coupling of each diamino acid 17 to compounds 10 by amide bond formation, using HATU and DIEA, to produce compounds 18.

G. Scheme 7

Resin 18 is treated with TFA/DCM to selectively remove the Boc protecting group on the diamino acid ligand to produce amines 19. The resin is then treated with one carboxylic acid reagent or one carboxyaldehyde (see Table 2) for either separate coupling of each carboxylic acid to compound 19 by amide bond formation or separate reductive amination of each carboxyaldehyde to compound 19 with sodium cyanoborohydride in methanol to produce resin 20.

H. Scheme 8

Compounds 20 are then treated with palladium tetrakistriphenylphosphine, tributyltin hydride in acetic acid and DCM to selectively remove the Alloc protecting group on the diamino acid ligand to produce amines 21. Each vessel is then treated with one carboxylic acid reagent (see Table 2) for separate coupling of the carboxylic acid to compounds 21 by amide bond formation to produce resin 22. Resin 22 may be cleaved by exposing the resin to UV light (ca. 360 nm) for 15–180 minutes at 25°–50° C. in a suitable solvent such as methanol to produce amides Formula I (wherein $R^2$ is H), as in Example 2 and Table 2.

I. Scheme 9

Diamino acid intermediate 23, one of the diamine ligands (Table 2), is prepared from hydroxy proline 24 by first treating it with alloxychloroformate, in a solvent such as water, in the presence of a base, e.g., potassium carbonate to yield Alloc protected compound 25. Compound 25 is esterified with either acid in methanol or diazomethane in diethyl ether, producing ester 26, which is then converted to bromide compound 27 using a brominating reagent such as triphenylphosphine and carbon tetrabromide. The bromide substituent is in turn displaced with azide using either sodium or potassium azide in DMF. Resultant azide compound 28 is then reductively alkylated with acetaldehyde, by first treating it with triphenylphosphine to generate an imine which is in turn reduced to an N-ethyl amino group in compound 29. Amine 29 is treated with Boc anhydride in acetonitrile to produce compound 30 which in turn is hydrolyzed to carboxylic acid compound 23 by the action of lithium hydroxide in water.

EXAMPLE 1

Entry 11, Table 1

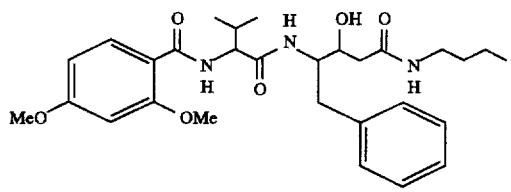

Step 1—Sequential Attachment of bis-Boc Lysine, Photo-labile Linker and an Amine 1a. Attachment of bis-Boc Lysine to TentaGel™

TentaGel™ resin (S-NH$_2$, 1.0 g, 0.029 mmol/g, 0.29 mmol, 180–220 um) was suspended in a solution of bis-Boc lysine (0.87 mmol, 0.5 g), and HOBt (0.87 mmol, 0.12 g), then treated with DIC (01.7 mmol, 0.27 mL). The suspension was shaken overnight, then drained and washed with 15 mL each DMF (3×), MeOH (3×) and DCM (3×).

1b. Removal of Boc Protecting Group and Attachment of Photo-labile Linker

A suspension of resin 1 (1.0 g) in 1:1 TFA/DCM was shaken for 1 hour, then washed with 50 mL each DCM (3×), MeOH (3×), 4:1 MeOH/Et$_3$N (1×), MeOH (3×), DMF (3×), then DCM (3×). This resin was then suspended in 25 mL DCM, then treated with a pre-incubated (45 min) solution of

11

4-bromomethyl-3-nitro benzoic acid (1.5 mmol, 0.40 g), HOBt (1.5 mmol, 0.23 g), DIC (3.2 mmol, 0.5 mL) in DCM (25 mL). The suspension was shaken for 3 hours, then drained and washed with three 50 mL portions of DCM.

1c. Addition of Amine

One gram of the step 1b resin was suspended in THF (50 mL) and then treated with butylamine (5.4 mmol) and shaken overnight. The resin was then drained and washed with 50 mL each DMF (3×), MeOH (3×), 10:1 MeOH/TFA (1×), MeOH (3×), DMF (3×), then DCM (3×).

Step 2—Addition of Phenylalanine-Derived Statine.

A suspension of the step 1c resin (1.0 g) in DMF (15 mL) was treated with the phenylalanine-derived Boc-protected statine (1.3 mmol), DIEA (2.6 mmol, 0.44 mL), then HATU (1.3 mmol, 0.5 g). This suspension was shaken for 6 hours, drained and washed with 15 mL portions of DMF (3×), MeOH (3×), DMF (3×), and DCM (3×). The dried resin 9 was divided into two portions.

Step 3—Deprotection and Attachment of Fmoc Valine

A suspension of resin 9 (0.5 g) in 40% TFA/DCM was shaken for 1 hour, then drained and washed with 50 mL each DCM (3×), MeHt (3×), 10% Et$_3$N/MeOH (1×), MeOH (3×), and DMF (3×). The product (0.5 g; 0.33 mmol) was suspended in 10 mL of DMF, containing Fmoc-valine (0.48 mmol) and HATU (0.48 mmol). The suspension was shaken at room temperature for 10 minutes and then DIEA (0.99 mmol) was added. The resulting mixture was shaken for 2 hours, continuously monitoring the resin from the vessel with the Kaiser test to determine the absence of amine functionality. Once the coupling was complete (Kaiser test negative), the resin was filtered and washed with 10 mL portions of DMF (3×), MeOH (3×) and DCM (3×).

Step 4—Fmoc-Deprotection.

The resin (0.5 g) was suspended in 30% piperidine in DMF (15 mL) and shaken for 1 hour at room temperature. The resin was filtered, washed with 15 mL portions of DMF (2×), DCM (3×), MeOH (3×) and DCM (5×), then dried under vacuum.

Step 5—Attachment of 2,4-dimethoxybenzoic acid

The resin in a reaction vessel was combined with 2,4-dimethoxybenzoic acid (0.6 mmol), HATU (0.72 mmol) and DIEA (1.8 mmol) in DMF (15 mL). The resulting suspension of resin was shaken for approximately one hour at room temperature, at which time the Kaiser test was negative. The resin was filtered and washed with 10 mL each DMF (2×), MeOH (3×) and DCM (5×). The resin was filtered and subjected to a wash cycle consisting of 10 mL portions each TFA/water (1:1) (2×), DMF (2×), MeOH (4×), DMF (2×) and DCM (5×), then dried in vacuum.

Step 6—Cleavage by light

The resin was suspended in MeOH (20 mL) and the compound cleaved from the resin at 50° C., then light (365 nm) was shone on them for 3 to 4 hours. The suspension was filtered, the MeOH removed to give the title compound as confirmed by mass spectroscopy (mass spectrum (fab): m/z=528 (MH$^+$)).

12

EXAMPLE 2

Entry 16, Table 2

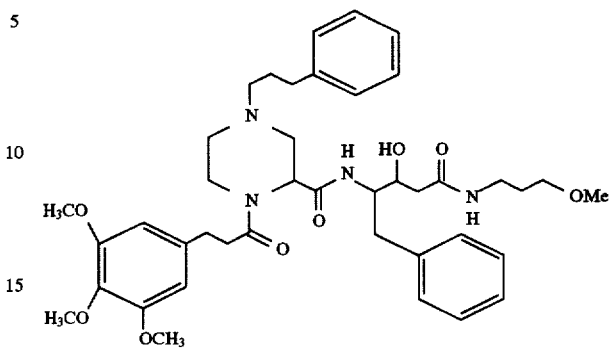

Step 1—Deprotection and Attachment of Diamino Acid

A suspension of resin 9 (0.5 g) in 40% TFA/DCM, prepared as in Example 1, with the exception that 3-methoxypropylamine was used in place of butylamine, was shaken for 1 hour, then drained and washed with 50 mL portions of DCM (3×), MeOH (3×), 10% Et$_3$N/MeOH (1×), MeOH (3×) and DMF (3×). A suspension of this resin in DMF (50 mL) was treated with the corresponding diamino carboxylic acid (entry 16, Table 2; 1.6 mmol), DIEA (3.3 mmol), then HATU (1.7 mmol). The suspension was shaken for 6 hours, then drained and washed with 50 mL portions of DMF (3×), MeOH (3×), DMF (3×), then DCM (3×) and filtered. The resin was dried in vacuo.

Step 2—Deprotection and Attachment of a Carboxyaldehyde

A suspension of resin batch one (0.5 g) in 40% TFA/DCM (10 mL) was shaken for 1 hour, then drained and washed with 10 mL portions of DCM (3×), MeOH (3×), 10% Et$_3$N/MeOH (1×), MeOH (3×), and DMF (3×). This resin, suspended in 2% HOAc/DMF (10 mL), was treated with 3-phenylpropionyl (8.8 mmol), followed by the addition of NaBH$_3$CN (4.4 mmol, 0.28 g). The resin was shaken overnight, then drained and washed with 10 mL portions of DMF (3×), MeOH (3×), then DMF (3×), DCM (3×). The resin was dried in vacuo.

Step 3—Deprotection and Attachment of 3-(2,3,4-Trimethoxyphenyl)Propionoic Acid

A suspension of resin (0.5 g) in DCM (10 mL) was treated with HOAc (4.8 mmol, 0.27 mL), Pd(PPh$_3$)$_4$ (0.072 mmol, 83 mg), then Bu$_3$SnH (2.4 mmol, 0.64 mL). This suspension was shaken for 1 hour, then drained and washed with 10 mL portions of DCM (3×), pyridine (3×), DCM (3×), then DMF (3×). The resin in DMF (10 mL) was then treated with 3-(2,3,4-trimethoxyphenyl)propionoic acid (0.36 mmol), followed by DIEA (0.72 mmol, 0.13 mL), and HATU (0.36 mmol, 0.14 g). This suspension was shaken for 6 hours, then drained and washed with 10 mL portions of DMF (3×), MeOH (3×), then DMF (3×) and DCM (3×).

Step 4—Cleavage by Light

The resin was suspended in MeOH (20 mL) and the compound cleaved from the resin at 50° C., then light (365 nm) was shone on them for 3 to 4 hours. The suspension was filtered, the MeOH removed to give the title compound as confirmed by mass spectroscopy (mass spectrum (fab): m/z=719 (MH$^+$)).

Using these methods, compounds in Tables 1 and 2 were prepared. The compounds in Tables 1 and 2 typically show greater than 2-fold selectivity for either plasmepsin or cathepsin D at an inhibitory activity (IC50) less than 10 micromolar.

TABLE 1

R Groups for Compounds of Formula I where Y is an amino acid

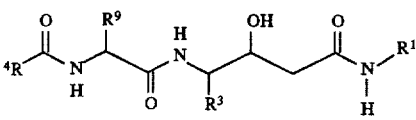

| Entry | $R^1$ | $R^3$ | $R^9$ | $R^4$ |
|---|---|---|---|---|
| 1 | butyl | $CH_2Ph$ | $CH(Me)CH_2Me$ | 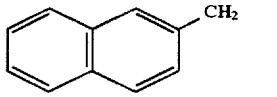 |
| 2 | butyl | $CH_2Ph$ | $CH(Me)CH_2Me$ | 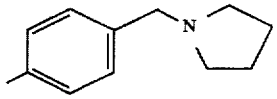 |
| 3 | 3-phenylpropyl | $CH_2Ph$ | $CH(Me)CH_2Me$ | 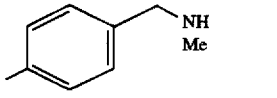 |
| 4 | butyl | $CH_2CH(Me)_2$ | $CH(Me)_2$ | octyl |
| 5 | 3-phenylpropyl | $CH_2CH(Me)_2$ | $CH(Me)CH_2Me$ | 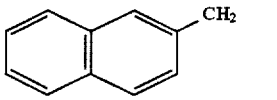 |
| 6 | 3-phenylpropyl | $CH_2CH(Me)_2$ | $CH(Me)CH_2Me$ | 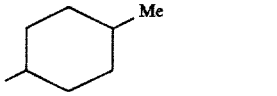 |
| 7 | butyl | $CH_2Ph$ | $CH(Me)_2$ | 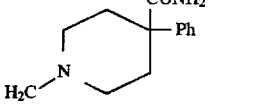 |
| 8 | 3-phenylpropyl | $CH_2Ph$ | $CH(Me)_2$ | 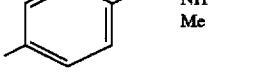 |
| 9 | 3-phenylpropyl | $CH_2Ph$ | $CH(Me)CH_2Me$ |  |
| 10 | 3-phenylpropyl | $CH_2Ph$ | $CH(Me)CH_2Me$ |  |
| 11 | butyl | $CH_2Ph$ | $CH(Me)_2$ |  |
| 12 | butyl | $CH_2CH(Me)_2$ | Ph | 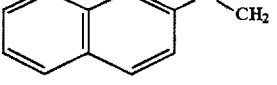 |

TABLE 1-continued

R Groups for Compounds of Formula I where Y is an amino acid

| Entry | $R^1$ | $R^3$ | $R^9$ | $R^4$ |
|---|---|---|---|---|
| 13 | 3-methoxypropyl | $CH_2CH(Me)_2$ | $CH_2SH$ | 2-methoxymethyl-naphthalene |
| 14 | butyl | $CH_2CH(Me)_2$ | $CH_2CH(Me)_2$ | 2-methoxymethyl-naphthalene |
| 15 | butyl | $CH_2CH(Me)_2$ | $CH_2Ph$ | 2-methoxymethyl-naphthalene |
| 16 | butyl | $CH_2CH(Me)_2$ | $CH_2$(2-thienyl) | 2-methoxymethyl-naphthalene |
| 17 | butyl | $CH_2Ph$ | Ph | 2-methylnaphthalene |
| 18 | butyl | $CH_2CH(Me)_2$ | $C(Me)_3$ | $(CH_2)_3-O-(2,4-di-Cl)Ph$ |
| 19 | 3-methoxypropyl | $CH_2Ph$ | Ph | $(CH_2)_3-O-(2,4-di-Cl)Ph$ |
| 20 | butyl | $CH_2Ph$ | Ph | 4-(OCH(COOH)$_2$)benzyl |
| 21 | butyl | $CH_2Ph$ | Ph | (2,4-di-OMe)phenyl |

TABLE 2

R Groups for Compounds of Formula I where Y is the diamino acid

| Entry | $R^1$ | $R^3$ | n | $R^6$ | $R^7$ |
|---|---|---|---|---|---|
| 1 | benzyl | Me | 0 | 3-pyridinylmethyl | 4-isopropoxybenzoyl |
| 2 | butyl | $CH_2Ph$ | 0 | $Ph(CH_2)_2O(CH_2)_2$- | (3,4,5-tri-OMe)benzoyl |
| 3 | butyl | $CH_2Ph$ | 0 | 4-phenylbenzyl | (3,4,5-tri-OMe)benzoyl |
| 4 | butyl | $CH_2Ph$ | 1 | (3,4,5-tri-OMe)benzyl | 4-isopropoxybenzoyl |
| 5 | butyl | $CH_2Ph$ | 1 | (4-MeC(O)NH)PhCH$_2$— | 3-phenoxybenzoyl |
| 6 | 3-phenylpropyl | $CH_2Ph$ | 0 | 4-phenylbutyl | (3,4,5-tri-OMe)benzoyl |
| 7 | butyl | $CH_2Ph$ | 0 | (4-MeC(O)NH)PhCH$_2$— | (3,4,5-tri-OMe)benzoyl |
| 8 | butyl | $CH_2Ph$ | 0 | 3,4-di-Cl-benzyl | (3,4,5-tri-OMe)benzoyl |
| 9 | butyl | $CH_2Ph$ | 0 | 4-phenylbenzyl | (3,4,5-tri-OMe)benzoyl |
| 10 | butyl | $CH_2Ph$ | 1 | (3,4,5-tri-OMe)benzyl | 3-phenoxybenzoyl |
| 11 | methyl | $CH_2Ph$ | 0 | 4-phenylbenzyl | 3-phenoxybenzoyl |
| 12 | 3-methoxypropyl | $CH_2Ph$ | 1 | 3,5-bis-trifluoromethylbenzyl | 4-isopropoxybenzoyl |

TABLE 2-continued

R Groups for Compounds of Formula I where Y is the diamino acid

| | | | | | |
|---|---|---|---|---|---|
| 13 | butyl | CH$_2$Ph | 0 | 3-phenylpropyl | (3,4,5-tri-OMe)benzoyl |
| 14 | methyl | CH$_2$Ph | 0 | 4-phenylbenzyl | 3-(2-OMe-phenyl)propyl |
| 15 | methyl | CH$_2$Ph | 0 | 3,4-di-Cl-benzyl | nicotinoyl |
| 16 | 3-phenylpropyl | CH$_2$Ph | 0 | 3-phenylpropyl | (3,4,5-tri-OMe-phenyl)propionyl |
| 17 | butyl | CH$_2$CH(Me)$_2$ | 0 | 3-phenylpropionyl | 3,3-diphenylpropionyl |
| 18 | 3-methoxypropyl | CH$_2$Ph | 0 | 4-phenylbenzyl | 3,3-diphenylpropionyl |
| 19 | butyl | CH$_2$Ph | 1 | 4-phenylbenzyl | 3,4-di-Cl-phenylacetyl |
| 20 | butyl | CH$_2$Ph | 0 | (3,4,5-tri-OMe)benzyl | (3,4,5-tri-OMe-phenyl)propionyl |
| 21 | methyl | CH$_2$Ph | 0 | 3,4-di-Cl-benzyl | EtOC(O)(CH$_2$)$_4$C(O)— |
| 22 | butyl | CH$_2$Ph | 0 | EtOC(O)(CH$_2$)$_4$C(O)— | 3,4,5-tri-OMe)benzoyl |

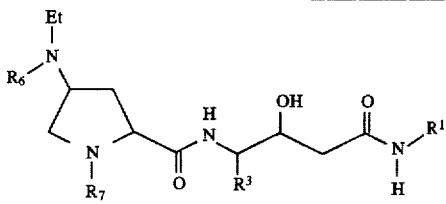

| Entry | R$^1$ | R$^3$ | R$^6$ | R$^7$ |
|---|---|---|---|---|
| 23 | butyl | CH$_2$Ph | 4-phenylbenzyl | phenylacetyl |
| 24 | 2-pyridinylmethyl | CH$_2$Ph | Me$_2$CHCH$_2$— | 3-phenoxybenzoyl |
| 25 | 3-pyridinylmethyl | CH$_2$CH(Me)$_2$ | propionyl | 3,3-diphenylpropionyl |
| 26 | 3-pyridinylmethyl | CH$_2$Ph | 3,5-di-CF$_3$-phenylacetyl | 3,3-diphenylpropionyl |

Scheme 1
Attachment of Bis-Boc lysine to resin

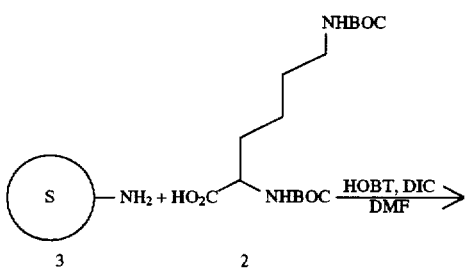

Scheme 2
Attachment of BNB linker and addition of amine

Step (1): BNB attachment:

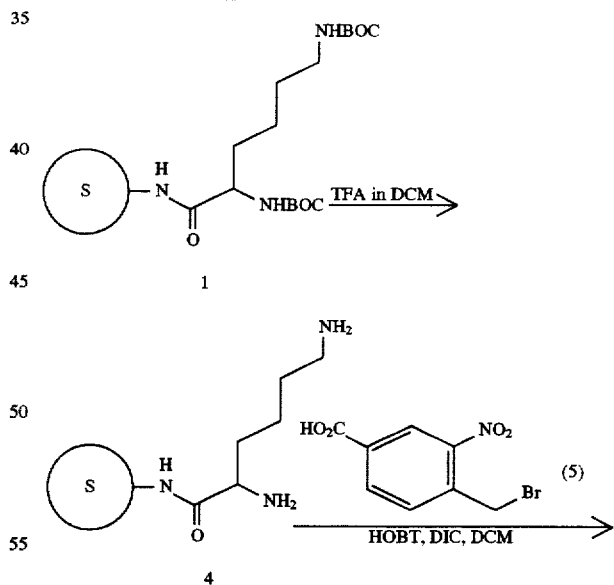

5,734,054

19

-continued
Scheme 2
Attachment of BNB linker and addition of amine

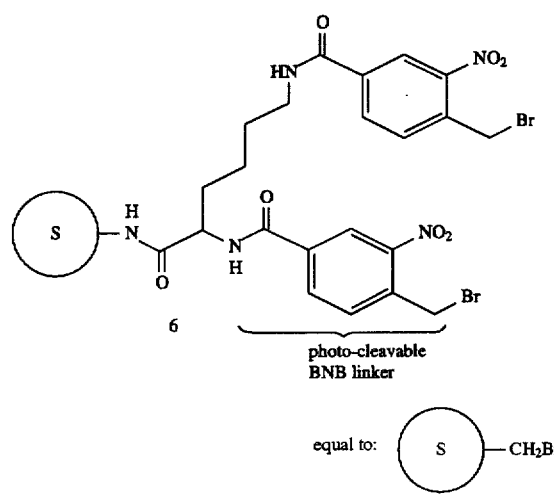

Step (2): Amine attachment:

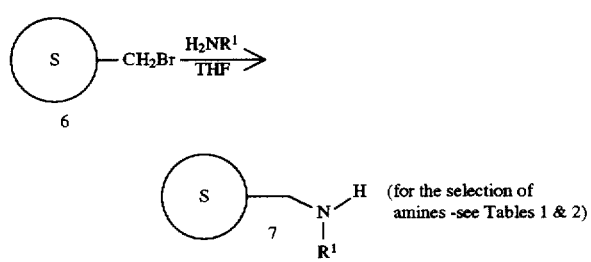

(for the selection of amines -see Tables 1 & 2)

Scheme 3
Attachment of hydroxy-amino acids

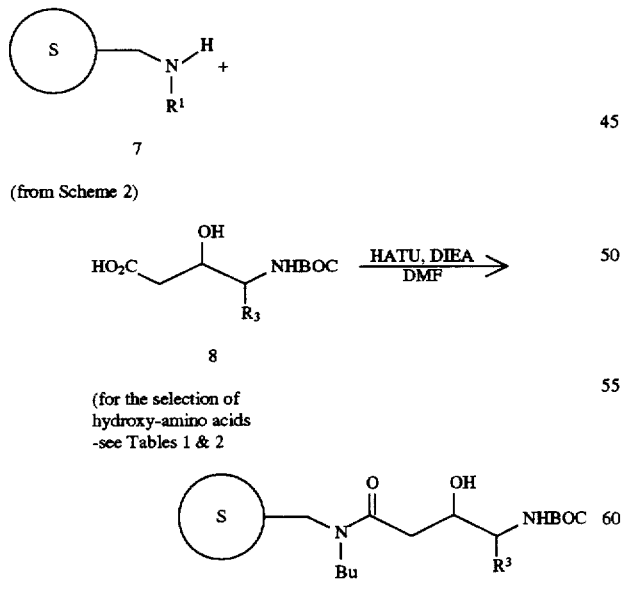

(for the selection of hydroxy-amino acids -see Tables 1 & 2

20

Scheme 4
Removal of BOC-protecting group and attachment of FMOC-amino acids

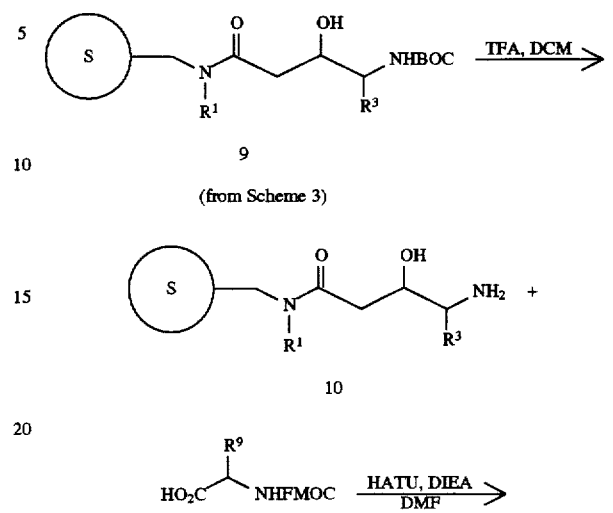

Scheme 5
Removal of FMOC-protecting group,
attachment of N-terminal $R^4$ groups and cleavage

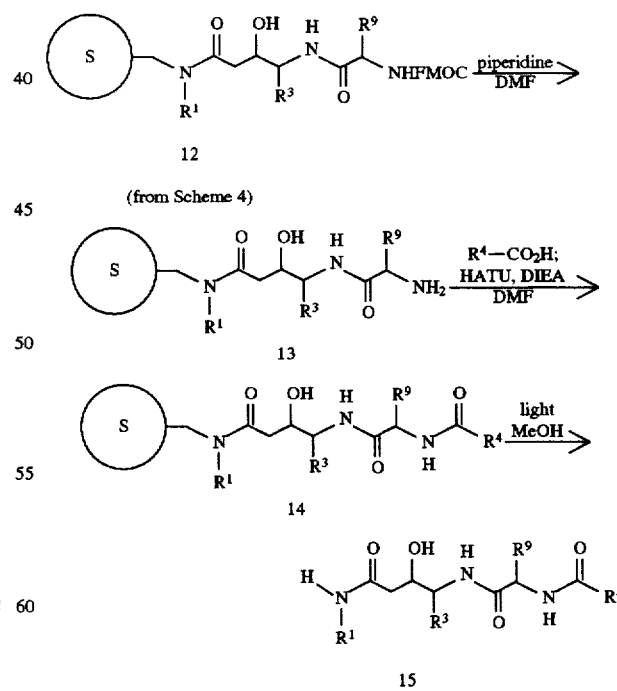

(See Example 1 and compounds in Table 1)

Scheme 6
Removal of BOC-protecting group and attachment of diamino acids

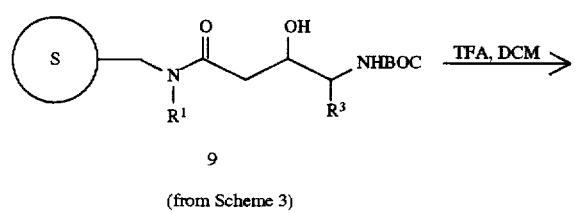

9

(from Scheme 3)

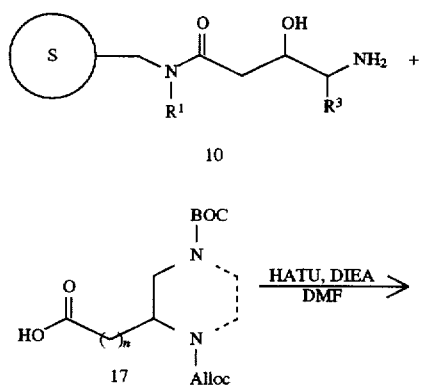

10

(for the selectin of diamino acids-see Table 2)

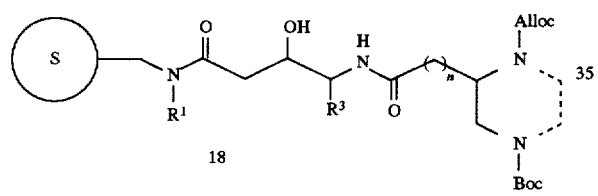

18

Scheme 7
Removal of the BOC-protecting group and acylation or reductive amination of secondary amine

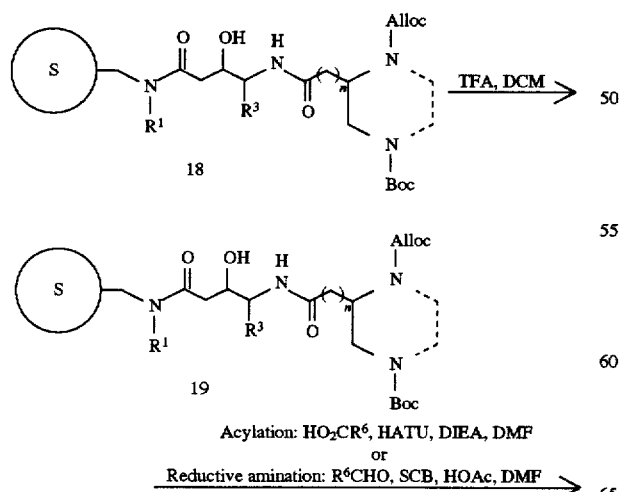

Acylation: HO₂CR⁶, HATU, DIEA, DMF
or
Reductive amination: R⁶CHO, SCB, HOAc, DMF

Scheme 7
Removal of the BOC-protecting group and acylation or reductive amination of secondary amine

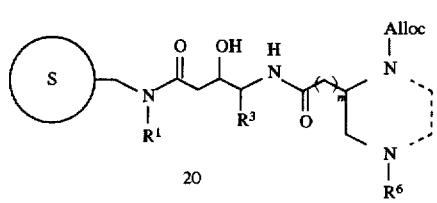

20

Scheme 8
Removal of the Alloc-protecting group and acylation of secondary amine

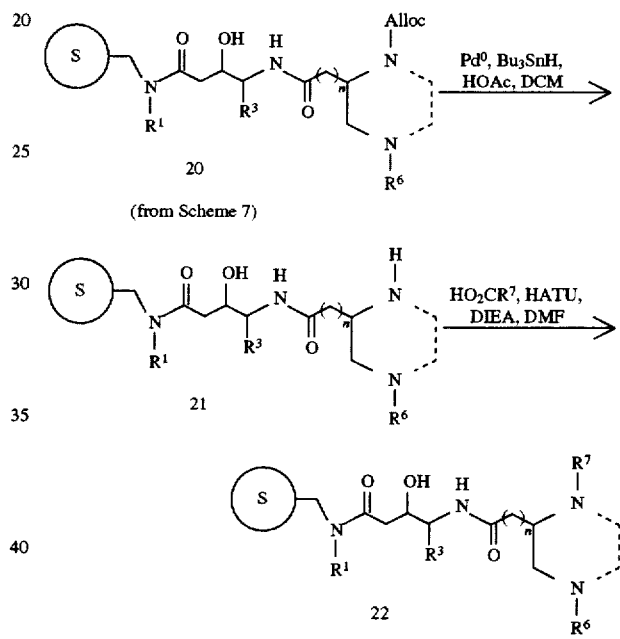

(library of Example and compounds of Table 2)

Scheme 9
Preparation of Carboxylic Acid 23

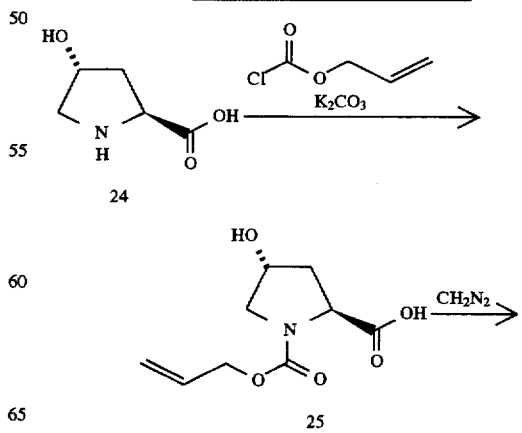

-continued
Scheme 9
Preparation of Carboxylic Acid 23

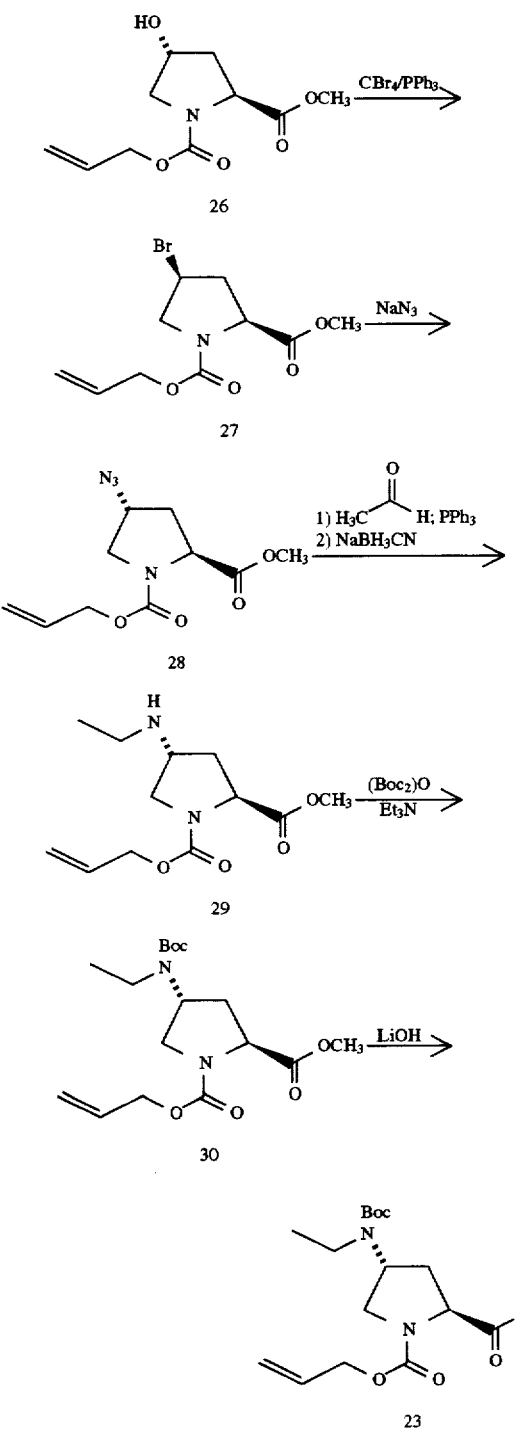

We claim:
1. A compound of Formula I

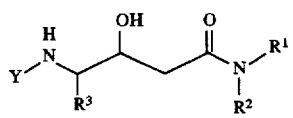

wherein:

R¹ and R³ are independently chosen from the group consisting of alkyl, alkoxyalkyl 2-pyridinylmethyl, 3-pyridinylmethyl and arylalkyl;

R² is H or ⓢ—C(O)—L—;

wherein:

ⓢ is a solid support; and

—L— is a linker of Formula (a)

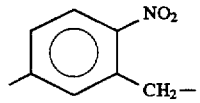

wherein the left-hand bond is the point of attachment to —C(O)— and the right-hand bond is the point of attachment to the amide nitrogen of Formula I; and Y is —C(O)R⁵ wherein R⁵ is

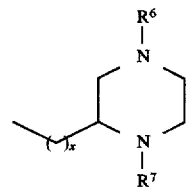

wherein x is 0 or 1; and

R⁶ and R⁷ are independently chosen from the group consisting of substituted alkyl, alkylcarbonyl and substituted alkylcarbonyl.

2. A compound according to claim 1 wherein R² is hydrogen.

3. A compound according to claim 2 wherein

R¹ is chosen from the group consisting of methyl, benzyl, butyl, 3-phenylpropyl, 3-methoxypropyl, 2-pyridinylmethyl and 3-pyridinylmethyl;

R⁶ is chosen from the group consisting of 3-pyridinylmethyl, phenylethoxyethyl, 3,4,5-trimethoxybenzyl, 4-acetamidobenzyl, 4-phenylbutyl, 3,4-dichlorobenzyl, 4-phenylbenzyl, 3-phenylpropyl, ethyl adipoyl, 3,5-bis(trifluoromethyl)benzyl, 3-phenylpropionyl, isobutyl, propionyl and 3,5-di(trifluoromethyl)phenylacetyl; and R⁷ is chosen from the group consisting of 4-isopropoxybenzoyl, nicotinoyl, 3,4,5-trimethoxybenzoyl, 3-phenoxybenzoyl, 3-(2-methoxyphenyl)propyl, 3,4,5-trimethoxyphenylpropionyl, 3,3-diphenylpropionyl, phenylacetyl, 3,4-dichlorophenylacetyl and ethyl adipoyl.

4. A compound according to claim 3 wherein

R¹ is chosen from the group consisting of methyl, benzyl, butyl, 3-phenylpropyl and 3-methoxypropyl;

R⁶ is chosen from the group consisting of 3-pyridinylmethyl, phenylethoxyethyl, 3,4,5-trimethoxybenzyl, 4-acetamidobenzyl, 4-phenylbutyl, ethyl adipoyl, 3,4-dichlorobenzyl, 4-phenylbenzyl, 3,5-bis(trifluoromethyl)benzyl, 3-phenylpropionyl and 3-phenylpropyl; and R⁷ is chosen from the group consisting of 4-isopropoxybenzoyl, nicotinoyl, 3,4,5-trimethoxybenzoyl, 3-phenoxybenzoyl, 3-(2- methoxyphenyl)propyl, 3,4,5-trimethoxyphenylpropionyl, 3,3-diphenylpropionyl, 3,4-dichlorophenylacetyl, and ethyl adipoyl.

5. A compound according to claim 1 wherein $R^2$ is (S)—C(O)—L—.

6. A compound according to claim 5 wherein:

$R^1$ is chosen from the group consisting of methyl, benzyl, butyl, 3-phenylpropyl, 3-methoxypropyl, 2-pyridinylmethyl and 3-pyridinylmethyl;

$R^6$ is chosen from the group consisting of 3-pyridinylmethyl, phenylethoxyethyl, 3,4,5-trimethoxybenzyl, 4-acetamidobenzyl, 4-phenylbutyl, 3,4-dichlorobenzyl, 4-phenylbenzyl, 3-phenylpropyl, ethyl adipoyl, 3,5-bis(trifluoromethyl)benzyl, 3-phenylpropionyl, isobutyl, propionyl and 3,5-di(trifluoromethyl)phenylacetyl; and $R^7$ is chosen from the group consisting of 4-isopropoxybenzoyl, nicotinoyl, 3,4,5-trimethoxybenzoyl, 3-phenoxybenzoyl, 3-(2-methoxyphenyl)propyl, 3,4,5-trimethoxyphenylpropionyl, 3,3-diphenylpropionyl, phenylacetyl, 3,4-dichlorophenylacetyl and ethyl adipoyl.

7. A compound according to claim 6 wherein $R^1$ is chosen from the group consisting of methyl, benzyl, butyl, 3-phenylpropyl and 3-methoxypropyl;

$R^6$ is chosen from the group consisting of 3-pyridinylmethyl, phenylethoxyethyl, 3,4,5-trimethoxybenzyl, 4-acetamidobenzyl, 4-phenylbutyl, ethyl adipoyl, 3,4-dichlorobenzyl, 4-phenylbenzyl, 3,5-bis(trifluoromethyl)benzyl, 3-phenylpropionyl and 3-phenylpropyl; and $R^7$ is chosen from the group consisting of 4-isopropoxybenzoyl, nicotinoyl, 3,4,5-trimethoxybenzoyl, 3-phenoxybenzoyl, 3-(2-methoxyphenyl)propyl, 3,4,5-trimethoxyphenylpropionyl, 3,3-diphenylpropionyl, 3,4-dichlorophenylacetyl and ethyl adipoyl.

\* \* \* \* \*

UNITED STATES PATENT AND TRADEMARK OFFICE
CERTIFICATE OF CORRECTION

PATENT NO. : 5,734,054
DATED : Mar. 31, 1998
INVENTOR(S) : Dolle, III et al.

It is certified that error appears in the above-identified patent and that said Letters Patent is hereby corrected as shown below:

Column 2, lines 30-40,

"$R^5$ is 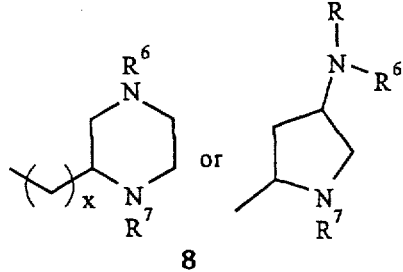 " should read -- $R^5$ is 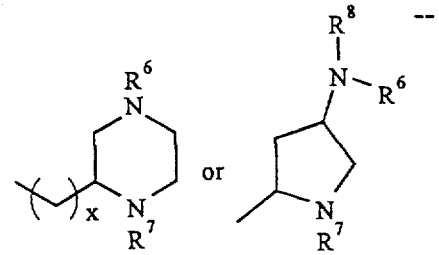 --

UNITED STATES PATENT AND TRADEMARK OFFICE
CERTIFICATE OF CORRECTION

PATENT NO. : 5,734,054

DATED : Mar. 31, 1998

INVENTOR(S) : Dolle, III et al.

Page 2 of 2

It is certified that error appears in the above-identified patent and that said Letters Patent is hereby corrected as shown below:

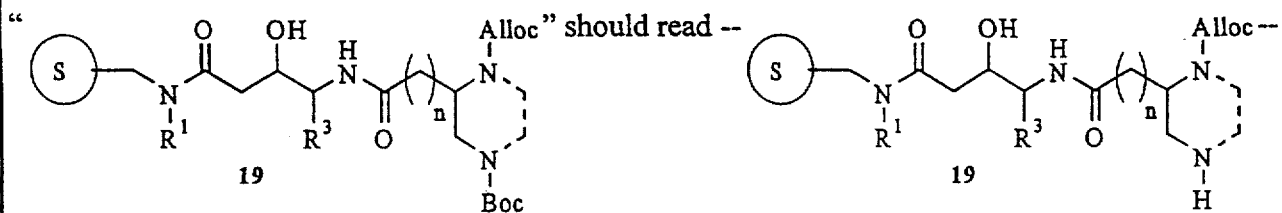

Signed and Sealed this

Third Day of November, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,734,054
DATED : Mar. 31, 1998
INVENTOR(S) : Dolle, III et al.

Page 1 of 2

It is certified that error appears in the above-identified patent and that said Letters Patent is hereby corrected as shown below:

Column 2, lines 30-40,

"$R^5$ is 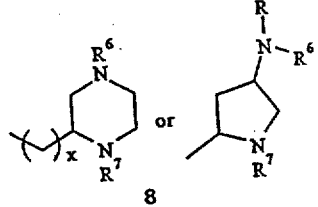 " should read -- $R^5$ is 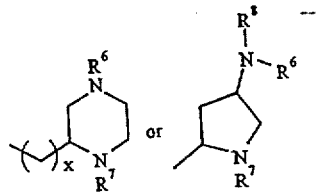 --

UNITED STATES PATENT AND TRADEMARK OFFICE
CERTIFICATE OF CORRECTION

PATENT NO. : 5,734,054
DATED : Mar. 31, 1998
INVENTOR(S) : Dolle, III et al.

Page 2 of 2

It is certified that error appears in the above-identified patent and that said Letters Patent is hereby corrected as shown below:

" Column 21, lines 55-62,

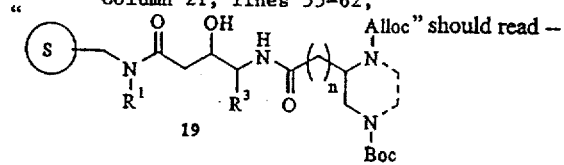 " should read -- 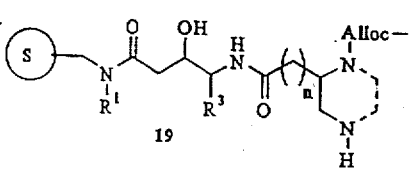

This certificate supersedes Certificate of Correction issued November 3, 1998.

Signed and Sealed this

First Day of June, 1999

Attest:

Q. TODD DICKINSON

Attesting Officer

Acting Commissioner of Patents and Trademarks